(12) United States Patent
Choi et al.

(10) Patent No.: US 9,433,564 B2
(45) Date of Patent: Sep. 6, 2016

(54) BIPHASIC COSMETIC

(71) Applicant: Restorsea, LLC, New York, NY (US)

(72) Inventors: Ri An Choi, Cerritos, CA (US); Enrique P. Alabata, Torrance, CA (US); Patricia S. Pao, New York, NY (US)

(73) Assignee: Restorsea, LLC, New York, NY (US)

( * ) Notice: Subject to any disclaimer, the term of this patent is extended or adjusted under 35 U.S.C. 154(b) by 0 days.

(21) Appl. No.: 14/707,369

(22) Filed: May 8, 2015

(65) Prior Publication Data

US 2015/0328087 A1    Nov. 19, 2015

Related U.S. Application Data

(60) Provisional application No. 61/994,616, filed on May 16, 2014.

(51) Int. Cl.
| | | |
|---|---|---|
| *A61K 8/03* | (2006.01) | |
| *A61K 8/97* | (2006.01) | |
| *A61Q 19/08* | (2006.01) | |
| *A61K 8/31* | (2006.01) | |
| *A61Q 19/00* | (2006.01) | |
| *A61K 8/98* | (2006.01) | |

(52) U.S. Cl.
CPC . *A61K 8/03* (2013.01); *A61K 8/31* (2013.01); *A61K 8/97* (2013.01); *A61K 8/975* (2013.01); *A61K 8/987* (2013.01); *A61Q 19/00* (2013.01); *A61Q 19/08* (2013.01); *A61K 2800/30* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 5,468,496 | A | 11/1995 | Touzan et al. |
| 5,510,120 | A | 4/1996 | Jones et al. |
| 5,587,168 | A * | 12/1996 | Vanonou ............. 424/401 |
| 6,019,991 | A | 2/2000 | Tanaka et al. |
| 6,346,245 | B1 | 2/2002 | Walther et al. |
| 6,376,557 | B1 | 4/2002 | Zaveri |
| 6,416,769 | B1 | 7/2002 | Vromen |
| 6,551,606 | B1 | 4/2003 | Golz-Berner et al. |
| 6,582,710 | B2 | 6/2003 | Deckers et al. |
| 6,592,866 | B2 | 7/2003 | Walther et al. |
| 6,599,513 | B2 | 7/2003 | Deckers et al. |
| 6,716,450 | B1 | 4/2004 | Yin et al. |
| 6,846,485 | B2 | 1/2005 | Bjarnason |
| 7,094,415 | B2 | 8/2006 | Marenick |
| 7,829,081 | B2 | 11/2010 | Bookbinder et al. |
| 8,075,920 | B2 | 12/2011 | Gammelsaeter et al. |
| 8,460,713 | B2 | 6/2013 | Gammelsaeter et al. |
| 8,557,295 | B2 | 10/2013 | Gammelsaeter et al. |
| 8,992,996 | B2 | 3/2015 | Alabata et al. |
| 2002/0064857 | A1 | 5/2002 | Walther et al. |
| 2003/0115686 | A1 | 6/2003 | Grey |
| 2004/0151684 | A1 | 8/2004 | Mori et al. |
| 2005/0075265 | A1* | 4/2005 | De Salvert et al. .......... 510/407 |
| 2005/0129739 | A1 | 6/2005 | Kohn et al. |
| 2005/0163872 | A1 | 7/2005 | Khare |
| 2006/0018867 | A1* | 1/2006 | Kawasaki et al. ....... 424/70.122 |
| 2006/0073211 | A1 | 4/2006 | Marenick et al. |
| 2006/0105005 | A1 | 5/2006 | Marenick et al. |
| 2006/0257386 | A1 | 11/2006 | Zimmerman et al. |
| 2006/0289834 | A1 | 12/2006 | Doisaki et al. |
| 2007/0074298 | A1 | 3/2007 | Kishimoto et al. |
| 2007/0243132 | A1 | 10/2007 | Russell-Jones et al. |
| 2008/0161229 | A1 | 7/2008 | Matsunaga et al. |
| 2009/0035240 | A1* | 2/2009 | Maes et al. ..................... 424/63 |
| 2009/0274770 | A1 | 11/2009 | Gammelsaeter et al. |
| 2010/0260695 | A1* | 10/2010 | Burke-Colvin et al. ........ 424/62 |
| 2011/0020302 | A1 | 1/2011 | Banov et al. |
| 2011/0027327 | A1 | 2/2011 | Albrecht |
| 2011/0097293 | A1 | 4/2011 | Grey et al. |
| 2011/0108049 | A1 | 5/2011 | Miyazaki et al. |
| 2011/0280882 | A1 | 11/2011 | Walther et al. |
| 2012/0082695 | A1 | 4/2012 | Asam |
| 2012/0107412 | A1 | 5/2012 | Gammelsaeter et al. |
| 2012/0123442 | A1 | 5/2012 | Larsen et al. |
| 2012/0288478 | A1 | 11/2012 | Florence et al. |
| 2012/0309689 | A1 | 12/2012 | Leren et al. |
| 2013/0028947 | A1 | 1/2013 | Albrecht |
| 2013/0129742 | A1 | 5/2013 | Walther et al. |

(Continued)

FOREIGN PATENT DOCUMENTS

| | | |
|---|---|---|
| AU | 2007200216 | 8/2007 |
| EP | 139468 B1 | 1/1990 |

(Continued)

OTHER PUBLICATIONS

CAS Common Chemistry. Registry No. 111-01-3, <http://www.commonchemistry.org/ChemicalDetail.aspx?ref=111-01-3>, accessed Jun. 19, 2015.*
Cosmetic Ingredient Analysis: Whitening Agents, http://www.brunswicklabs.com/whitening-agents, available May 23, 2010; accessed Jun. 19, 2015.*
AA2G stabilised vitamin C from Hayashibara. Hayashibara International, Inc., Apr. 1, 2003.
Aqua Bio Technology ASA, Aquabeautine XL brochure, 6 pages, dated Dec. 2011.
Aqua Bio Technology, Aquabeautine XL®—The Natural and Gentle Skin Refinisher [online], retrieved on Apr. 25, 2014. Retrieved from the Internet: http://www.aquabiotechnology.com/index.php?id=5.

(Continued)

*Primary Examiner* — Ileana Popa
*Assistant Examiner* — Nicole Babson
(74) *Attorney, Agent, or Firm* — Fish & Richardson P.C.

(57) ABSTRACT

A bi-phasic, non-emulsion cosmetic composition for application to skin includes a hydrophobic liquid phase and a hydrophilic liquid phase separate from but in contact with the hydrophobic liquid phase. Either or both phases may include active ingredients useful for cosmetic applications. When the composition is agitated, a temporary mixture of the two phases results, wherein the mixture contains globules of one of the phases suspended in the other. The mixture containing globules is applied to skin as a cosmetic.

28 Claims, No Drawings

(56) References Cited

U.S. PATENT DOCUMENTS

| | | | |
|---|---|---|---|
| 2013/0202581 A1 | 8/2013 | Fallon et al. |
| 2013/0261063 A1 | 10/2013 | Gammelsaeter et al. |
| 2013/0336948 A1 | 12/2013 | Alabata et al. |
| 2014/0037752 A1 | 2/2014 | Gammelsaeter et al. |
| 2014/0072547 A1 | 3/2014 | Alabata et al. |
| 2014/0220088 A1 | 8/2014 | Walther et al. |
| 2014/0275289 A1 | 9/2014 | Weisman et al. |
| 2015/0165002 A1 | 6/2015 | Alabata et al. |

FOREIGN PATENT DOCUMENTS

| | | |
|---|---|---|
| EP | 0370856 | 5/1990 |
| EP | 0603080 | 6/1994 |
| EP | 1089704 B1 | 2/2004 |
| EP | 1397200 B1 | 4/2007 |
| JP | 2009207473 | 9/2009 |
| JP | 201065048 | 3/2010 |
| KR | 1020050083960 | 8/2005 |
| KR | 20080059066 | 6/2008 |
| WO | WO99/29836 | 6/1999 |
| WO | WO0007627 | 2/2000 |
| WO | WO2010042399 | 4/2010 |
| WO | WO2010049688 | 5/2010 |
| WO | WO2011006434 | 1/2011 |
| WO | WO2011006508 | 1/2011 |
| WO | WO2011064384 | 6/2011 |
| WO | WO2011135059 | 11/2011 |
| WO | WO2012175742 | 12/2012 |
| WO | WO2012175743 | 12/2012 |
| WO | WO2013078259 | 5/2013 |
| WO | WO2013112569 | 8/2013 |
| WO | WO2014091312 | 6/2014 |
| WO | WO2014094918 | 6/2014 |
| WO | WO2014096187 | 6/2014 |

OTHER PUBLICATIONS

Bai et al., "Toxicity of zinc oxide nanoparticles to zebrafish embryo: a physicochemical study of toxicity mechanism," J Nanopart Res., 2010;12:1645-1654.

Bedford, Robert F., NDA 19-617/S027—Diprivan (propofol) Injectable Emulsion Apr. 26, 1996.

Biotechmarine (R), "Kalpariane (R) ," www.labo-esthesante.fr/minexcell28/pdf/7726_2.pdf, Aug. 13, 2008.

Blue Plasma, http://www.perriconemd.com/product/blue+plasma.do, Oct. 7, 2012.

Bumble and bumble Products, LLC, Concen-Straight Smoothing Treatment, Mar. 31, 2012, learn where and how to buy at Bumbleandbumble.com.

Chantasart et al., "Structure Enhancement Relationship of Chemical Penetration Enhancers in Drug Transport across the Stratum Corneum," Pharmaceutics, Jan. 17, 2012;4:71-92. doi: 10.3390/pharmaceutics4010071.

Cho et al., "The Antioxidant Properties of Brown Seaweed (*Sargassum siliquastrum*) Extracts," J Med Food, 2007;10:479-485.

Cowan, M.M., "Plant Products as Antimicrobial Agents," Clinical Microbiology Reviews, Oct. 1999;12(4)564-582.

Coste, F., Multi-functional Marine Active Ingredient as a Gentle Alternative to AHAs, http://www.google.com/url?url=http://www.in-cosmetics.com/novadocuments/11186&rct=j&frm=1&q=&esrc=s&sa=U&ei=avsRVPL1MM6PyASA1ILABg&ved=0CC0QFjAI&sig2=nytjK8ymfCWZGJGhNxrEdA&usg=AFQjCNGWxmhHbdcOMJ0pjVA1-xwC26FF0w, Apr. 2012, p. 9,10,25.

Franklin et al., "Comparative Toxicity of Nanoparticulate ZnO, Bulk ZnO, and ZnC12 to a Freshwater Microalga (*Pseudokirchneriella subcapitata*): The Importance of Particle Solubility," Environ. Sci. Technol., 2007;41:8484-8490.

Hare (SA Pharmacists's Assistant (Summer 2007) p. 30).

http://plants.usda.gov/core/profile?symbol=LOJA (accessed Oct. 31, 2013).

International Search Report and Written Opinion for App. Ser. No. PCT/US2014/070126, mailed Mar. 31, 2015.

Karasakai et al., Determination of vitamin e (o-tocopherol) in canola oils by high performance liquid chromatography, Planta Medica, 2011;77:PA28.

"Omega-3,6, and 9 and How They Add Up," (http://www.uccs.edu/Documents/peakfood/hlthTopics/Omega-3_6_and_9_Fats.pdf).

LEX—Ground Breaking Natural Multifunctional Technology for Age Management and Improvement of Skin Appearance, http://www.regenics.no/filer/cosmetics.htm, Mar. 4, 2013.

Lonne, GK et al., "Composition Characterization and Clinical Efficacy Study of a Salmon Egg Extract," Int J Cosmet Sci., Oct. 2013;35(5):515-22.

Orsetti, Valeria, thesis: "Molecular Studies of Piscine Hatching Enzymes," http://tesi.cab.unipd.it/14043/1/Orsetti_Valeria.pdf, 2007.

Packman and Gans, Topical moisturizers: quantification of their effect on superficial facial lines, J. Soc. Cosmet. Chem., 29, 79-90 (1978).

Perricone MD, Blue Plasma [online], retrieved on Apr. 25, 2014. Retrieved from the Internet: http://www.perriconemd.com/product/blue+plasma.do.

Prospectus of Aqua Bio Technology ASA; Dec. 2007.

Restorsea 24kt Liquid Gold Face Oil product description and ingredients [online], [retrieved on May 4, 2015]. Retrieved from the Internet: http://www.restorsea.com/dp/B00LU20LO2, 6 pages.

Restorsea Exfoliating Scalp Treatment product description [online], retrieved on Apr. 7, 2015. Retrieved from the Internet: http://www.restorsea.com/dp/B00JFHXEOS.

Restorsea product brochure, Oct. 2014.

Restorsea product brochure, May 29, 2014.

Restorsea LLC, The Restorsea 3-Step Regimen [online], retrieved on Apr. 25, 2014. Retrieved from the Internet: http://www.restorsea.com/info/Regimen_Offer.

The Restorsea 3-Step Regimen, http://www.restorsea.com/info/Regimen_Offer#tabs, Jul. 1, 2014.

Restorsea Revitalizing Eye Cream, 0.5oz 0-5oz—Bergdorf Goodman [online], retrieved on Apr. 25, 2014. Retrieved from the Internet: http://www.bergdorfgoodman.com/Restorsea-Revitalizing-Eye-Cream-0-5oz-restorsea/prod97540004_/p.prod?icid=&searchType=MAIN&rte=%252Fsearch.jsp%253FN%253D0%2526Ntt%253Drestorsea%2526_requestid%253D43404&eItemId=prod97540004&cmCat=search.

Restorsea Rolls Out 24-Karat Gold Face Oil (Oct. 2, 2014) [online], [retrieved on Apr. 6, 2015]. Retrieved from the Internet: http://www.happi.com/issues/2014-10-01/view_breaking-news/restorsea-rolls-out-24-karat-gold-face-oil/, 6 pages.

Screenshot of http://www.amil.com.pl/?id=25&mod=&tpl=&_action= (machine translation), Aug. 12, 2009.

Screenshot of http://www.apothekenbote.at/zona-sensitive-creme-75ml.html (machine translation), Jul. 2007.

Screenshot of http://www.mediconline.se/hudvard/problemhud/zona-byter-namn-till-z-skin-repair-c-160-1.aspx (machine translation), Sep. 30, 2011.

Screenshot of nordicexpressions.org/zona.htm ZSkinRepairSeries1.pdf Oct. 31, 2007 (The Z Skin Repair Series for problem Skin).

Screenshot of nordicexpressions.org/zona.htm ZSkinRepairSeries2.pdf Oct. 31, 2007 (Z Skin Repair and Zonase—a patented solution for problem skin).

Screenshot of nordicexpressions.org/zona.htm ZSkinRepairSeries3.pdf Oct. 31, 2007 (Z Skin Repair Extra Intensive Cream).

Screenshot of nordicexpressions.org/zona.htm ZSkinRepairSeries4.pdf Oct. 31, 2007 (Z Skin Repair Kids Sensitive Cream).

Screenshot of nordicexpressions.org/zona.htm ZSkinRepairSeries5.pdf Oct. 31, 2007 (Z Skin Repair Shampoo).

Screenshot of nordicexpressions.org/zona.htm ZSkinRepairSeries6.pdf Oct. 31, 2007 (Z Skin Repair Scalp Lotion Spray).

Screenshot of nordicexpressions.org/zona.htm ZSkinRepairSeries7.pdf Oct. 31, 2007 (Z Skin Repair Hand & Nail Cream).

Screenshot of nordicexpressions.org/zona.htm ZSkinRepairSeries8.pdf Oct. 31, 2007 (Z Skin Repair Lip Balm).

Screenshot of http://nordicexpressions.org/z_skin_repair.htm; Nov. 26, 2013.

(56) References Cited

OTHER PUBLICATIONS

Screenshot of shopping4net.se/HaelsokosWaard-hygien/Salvor/Zona-Sensitive.htm (machine translation) Nov. 27, 2007.
StyleBistro: Are Scalp Treatments the Next Big Thing in Haircare? (Apr. 30, 2014) [online], retrieved on Apr. 6, 2015. Retrieved from the Internet: http://www.stylebistro.com/Hair+Trend+Report/articles/28bV4YWOIV1/Scalp+Treatments+Next+Thing+Haircare.
Wang et al., "Total phenolic compounds, radical scavenging and metal chelation of extracts from Icelandic seaweeds," Food Chemistry, 2009;116: 240-248.
Warner et al., "Release of Proteases from Larvae of the Brine Shrill Artemia Franciscana and Their Potential Role During the Molting Process," Comp Biochem Physiol B-Biochem. Mol. Biol. Feb. 1998;119(2):255-63.
Warner et al., "Water Disrupts Stratum Corneum Lipid Lamellae; Damage is Similar to Surfactants," J Invest Dermatol., Dec. 1999;113:960-966.
Yasumasu et al., "Isolation and Some Properties of Low Choriolytic Enzyme (LCE), a Component of the Hatching Enzyme of the Teleost, Oryzias latipes," J Biochem., Feb. 1989;105:212-218.
Z Skin Repair Intensive Cream Electi Medicals, <http://www.halsans.com/en/body-care/skin-hair-nail-products/z-skin-repair-intensive-cream>; <http://nordicexpressions.org/z_skin_repair.htm>, Sep. 2014.
ZONA™ Extra Skin Repair [online], retrieved on Apr. 25, 2014. Retrieved from the Internet: http://www.amil.com.pl/?id=51&mod=&tpl=&_action=.
ZONA™ Sensitive [online], retrieved on Apr. 25, 2014. Retrieved from the Internet: http://www.amil.com.pl/?id=52&mod=&tpl=&_action=.
ZONA™ Shampoo [online], retrieved on Apr. 25, 2014. Retrieved from the Internet: http://www.amil.com.pl/?id=53&mod=&tpl=&_action=.
Al-Edresi et al., "Formulation and stability of whitening VCO-in-water nano-cream," *Int J Pharm.*, 2009;373:174-178.
Clarins Intensive Serum Bi-Phase, Mintel, Sep. 2009. Database GNPD [online], XP-002742003, Database accession No. 1172601.
MedicOnline, Z Skin Repair Scalp Tincture 75ml, Accessed May 16, 2015, Online at: translate.google.com/translate?hl=en&sl=sv&u=http://www.mediconline se/z-skin-repair-scalp-tincture-75ml-p-321-c-110.aspx&prev=search.
Pillai et al., "1,2-Alkanediols for Cosmetic Preservation," Cosmetics & Toiletries (Oct. 1, 2008) [online] [retrieved on Aug. 19, 2015]. Retrieved from the Internet: http://www.cosmeticsandtoiletries.com/formulating/function/preservatives/premium-12-alkanediols-for-cosmetic-preservation-228198361.html, 7 pages.
Schaefer, K., "Broad-spectrum Alternative to Caprylyl Glycol Preservative Blends," Cosmetics & Toiletries (Jan. 19, 2012) [online] [retrieved on Aug. 19, 2015]. Retrieved from the Internet: http://www.cosmeticsandtoiletries.com/formulating/function/preservatives/137670898.html , 2 pages.
Symrise Sensory Ingredients, Sensory News, Oct. 2005, 2 pages.
Supplementary European Search Report for App. Ser. No. EP 13 74 0793, dated May 8, 2015, 3 pages.
Truth in Aging, Glucosyl Hesperidin, Mar. 9, 2009, Available online on or before Oct. 24, 2012, as evidenced by Internet Archive Wayback machine, at: www.truthinaging.com/ingredients/glucosyl-hesperidin.
U.S. Food & Drug Administration, Appendix—Chelation potential of disodium EDTA [online] [retrieved on Aug. 19, 2015]. Retrieved from the Internet: http://www.fda.gov/downloads/Drugs/GuidanceComplianceRegulatoryInformation/ucm117682.pdf, 2 pages.
"Z Skin Repair Scalp Tincture 75 ml" (Google Translate from Swedish to English), Retrieved from the Internet on Aug. 15, 2015: https://translate.google.com/translate?hl=en&sl=sv&u=http://www.mabrapostorder.se/se/z-skin-repair-scalp-tincture-75-ml.php&prev=search, 1 page.
International Search Report and Written Opinion for App. Ser. No. PCT/US2015/029853, mailed Jul. 29, 2015.

\* cited by examiner

BIPHASIC COSMETIC

RELATED APPLICATIONS

This application claims priority benefit of U.S. Provisional Application Ser. No. 61/994,616, filed May 16, 2014, the contents of which are hereby incorporated by reference.

FIELD OF THE INVENTION

The present invention in general relates to a cosmetic composition, and in particular to a biphasic cosmetic composition containing enzymes and formulations thereof.

BACKGROUND OF THE INVENTION

Oils and mixtures of oils have long been used for moisturizing skin. In particular, skin that is dry, wrinkled, or rough is rendered more flexible and smooth to the touch by treatment with oils.

The application of oil, while bringing appreciable softness, a shiny appearance, and a protective effect to the skin, is not fully satisfactory as a cosmetic, owing to problems such as an unpleasant greasy and heavy feel. Further, while oils can deliver hydrophobic active agents into skin, they are limited in their ability to carry hydrophilic active agents.

In order to address these limitations of oil-based compositions, the industry sometimes incorporates oil into water-in-oil or oil-in-water emulsions in which surfactants are employed to produce a stable structure of minority phase droplets within a majority phase. The skin feel of an emulsified product is greatly improved compared to that of oil alone, and such a product has the ability to deliver both hydrophilic and hydrophobic ingredients to the skin. The stability of an emulsion affects skin penetration rates of active agents delivered by the product.

Many different water-soluble components can be added to a cosmetic. One class of water-soluble proteins that have been shown to improve skin quality are proteins associated with fish egg hatching. The observation of fish hatchery workers whose hands had exceptional skin quality even with prolonged exposure to cold water was the genesis of the isolation of a new class of proteins associated with hatching fish eggs. Such proteins are detailed in, for example, U.S. Pat. No. 6,346,245; U.S. Pat. No. 6,592,866; U.S. Pat. No. 8,992,996; US2011/0280882; WO2011/06434; and US2009/0274770. The proteins associated with the egg hatching process included serine proteases (e.g., zonases), lectins, very acidic proteins (VAPS) and choriolysins. Fish spawn isolate proteins have been included in oil/water emulsion-based cosmetic compositions, although maintaining enzymatic activity through the emulsification process is a technical challenge.

Thus, there exists a need for a non-emulsion, bi-phasic cosmetic composition that can simultaneously deliver aqueous-based and oil-based ingredients to skin. Such a composition should deliver the components of each phase in a way that retains the benefits of each. There further exists a need for such a cosmetic that is essentially free of synthetic cosmetic components that have unintended deleterious effects on the skin and bioaccumulation problems.

SUMMARY OF THE INVENTION

A bi-phasic, non-emulsion cosmetic composition for application to skin includes a hydrophobic liquid phase and a hydrophilic liquid phase separate from and having a meniscus in in contact with the hydrophobic phase. The hydrophilic liquid phase includes a suspending agent. A first active agent is provided in either the hydrophobic liquid phase or the hydrophilic liquid phase. When the composition is agitated, it forms globules of one of the phases suspended in the other phase. The globule-containing composition is then applied to skin.

A bi-phasic, non-emulsion cosmetic composition for application to skin is also provided that includes a hydrophobic liquid phase, the majority of which by volume is squalane, and, in contact with the hydrophobic liquid phase, a hydrophilic liquid phase, the majority of which by volume is water. A protein is present in the hydrophilic liquid phase as an active agent for improving skin quality. When the two phases are vigorously mixed at the time of application to skin (e.g., just prior to being applied to skin), globules are formed in the composition.

A biphasic, non-emulsion cosmetic composition is also provided that includes a hydrophobic phase in contact with an aqueous hydrophilic phase, wherein the hydrophobic phase includes squalane, an algae extract, and caprylic/capric triglyceride; and the aqueous hydrophilic phase includes the following: *sclerotium* gum; *Lactobacillus* fermentation filtrate; polyepsilon-lysine; ascorbyl glucoside; *Crocus sativus* flower extract; salmon hatching fluid filtrate; and a particulate comprising gold flecks and inorganic glitter formed of titanium dioxide, tin oxide, iron oxide, and either fluorophlogopite or mica.

A process for applying a protein or active ingredient to skin is also provided that includes providing one of the bi-phasic, non-emulsion cosmetic compositions disclosed herein, agitating the composition to form a mixture containing globules of the hydrophobic phase suspended in the hydrophilic phase, and applying the globule-containing mixture to skin.

A process for preparing a bi-phasic, non-emulsion cosmetic composition is provided, the process including providing a hydrophobic liquid phase and a separate hydrophilic liquid phase, wherein at least one of the two phases contains an active ingredient that is cosmetically active on the skin. Both phases are introduced into a container to form a bi-phasic, non-emulsion cosmetic composition with one phase layered on the other. Agitation of the composition produces globules of one of the liquid phases suspended in the other phase. The globule-containing product is then applied to skin.

DESCRIPTION OF THE INVENTION

The present invention has utility as a cosmetic with skin restorative attributes. In one embodiment, an inventive cosmetic is formulated as biphasic liquid that, upon agitation, forms globules for delivery to a user's skin. It has been surprisingly found that the performance of the biphasic cosmetic so applied to skin (i.e., after agitation to form globules) is altered, relative to conventional emulsions or to sequential application of separate oil-based and water-based formulations. Active agents for improving skin may be provided in either or both phases of an inventive biphasic cosmetic. In some embodiments, particles are suspended in either or both phases, e.g., to modify the reflectivity of skin after application of an inventive cosmetic to skin.

As used herein, skin quality assessment is readily performed by at least one measure of fine lines and wrinkles: Packman, E. W. and Gans, E. H. J. Soc. Cosmet. Chem., 29, 79-90 (1978); skin color by chroma meter measurements; and skin surface hydration by CORNEOMETER® measurements (Courage and Khazaka). Also useful is photography with standard light, ultraviolet light, cross-polarization and parallel polarization imaging.

It is to be understood that in instances where a range of values is provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

A hydrophobic phase is readily formed according to the present invention with a variety of skin compatible compounds. The hydrophobic phase forms a meniscus with deionized water at 20° C. A hydrophobic liquid phase may be formed from terpenes, terpene alcohols, sterols, vegetable oils, animal oils, silicone oils, mineral oils (paraffin oils), glycerides and combinations thereof. Examples of skin compatible compounds illustratively includes terpenes, such as squalene; hydrogenated forms of terpenes, such as squalane; terpene alcohols, such as geraniol, rhodinol, or farnesol; sterols; vegetable oils, such as almond oil, ambadi seed oil, argan oil, avocado oil, canola oil, cashew oil, castor oil, coconut oil, corn oil, cottonseed oil, grape seed oil, hazelnut oil, hemp oil, linseed oil (flaxseed oil), macadamia oil, manila oil, mongongo nut oil, mustard oil, olive oil, palm oil, palm kernel oil, peanut oil, pecan oil, *perilla* oil, pine nut oil, pistachio oil, poppyseed oil, pumpkin seed oil, rapeseed oil, rice bran oil, safflower oil, sesame oil, soybean oil, sunflower seed oil, tea seed oil, walnut oil, or watermelon seed oil; animal oils such as lard oil, animal hoof oil, tuna oil, seal oil, egg oil, sheep oil, turtle oil, halibut liver oil, marmot liver oil, or cod liver oil; silicones such as polydimethoxylsilicone or siloxanes; or combinations thereof.

The hydrophobic liquid phase is typically present from 5 to 95 volume percent of the cosmetic, with the remainder being hydrophilic liquid phase (with or without suspended solid particles in one or both phases). In other embodiments, the hydrophobic liquid phase is present from 25 to 60 volume percent. For the purpose of calculating phase volumes in the biphasic cosmetic, the volume of each of the two phases is inclusive of any dissolved or suspended components in the respective phase. In certain inventive embodiments, the hydrophobic phase does not contain synthetic substances. In other inventive embodiments, the hydrophobic phase does not contain detergents or foaming agents.

Substances can be readily dissolved or suspended in the hydrophobic liquid phase. These substances illustratively include anti-oxidizing agents, coloring agents, perfumes, biocides, particulates, active agents intended to improve skin quality or appearance, skin moisturizers, and combinations thereof.

Hydrophobic active agents operative herein illustratively include essential oils, capric triglycerides, caprylic triglycerides, oil-soluble plant extracts or algae extracts such as those derived by carbon dioxide extraction or oil extraction from plants or algae such as *Alaria Esculenta, Rhododendron ferrugineum, Amaranthus caudatus, Angelica archangelica, Pimpinella anisum, Malus domestica, Mentha suaveolens,* Oat avenanthramide, *Prunus armeniaca, Arnika montana, Cynara scolymus, Asparagus officinalis, Persea americana, Cardiospermum halicacabum, Melissa officinalis, Bambusa vulgaris, Musa paradisiaca, Adansonia digitata, Berberis vulgaris, Ocimum basilicum, Laurus nobilis, Epilobium angustifolium, Allium ursinum, Geum urbanum, Betula pubescens, Quassia amara, Nigella sativa, Ribes nigrum, Moms nigra, Raphanus sativus, Camellia sinensis, Rubus fruticosus, Iris versicolor, Vaccinium myrtillus, Borago officinalis, Vicia faba, Menyanthes trifoliata, Fagopyrum esculentum, Arctium lappa, Ruscus aculeatus, Theobroma cacao,* Acorns *calamus, Carum carvi, Elettaria cardamomum, Daucus carota sativus, Erythroxylum catuaba, Centaurium erythraea, Matricaria chamomilla, Prunus cerasus, Cicer arietinum, Chlorella vulgaris, Aronia melanocarpa, Cinchona pubescens, Cinnamomum verum, Syzygium aromaticum, Cocos nucifera, Coffea arabica, Plectranthus barbatus, Tussilago farfara, Symphytum officinale, Plantago major, Coriandrum sativum, Zea mays, Papaver rhoeas, Centaurea cyanus, Gossypium herbaceum, Vaccinium vitis-idaea, Primula veris, Vaccinium macrocarpon, Cucumis sativus, Curcuma longa, Bellis perennis, Rosa damascena, Turnera diffusa, Taraxacum officinale, Phoenix dactylifera, Lamium album, Rosa canina, Hylocereus undatus, Daemonorops draco, Echinacea angustifolia, Leontopodium alpinum, Sambucus nigra, Acanthopanax senticosus, Phyllanthus emblica, Eucalyptus globulus, Oenothera biennis, Helichrysum arenarium, Euphrasia rostkoviana, Trigonella foenum-graecum, Ficus carica, Linum usitatissimum, Plumeria alba, Fumaria officinalis, Rumex acetosa, Gardenia Jasminoides, Gentiana lutea, Zingiber officinale, Ginkgo biloba, Panax ginseng, Solidago virgaurea, Vitis vinifera, Citrus paradisi, Camellia sinensis, Paullinia cupana, Graminis flos, Corylus avellana, Lawsonia inermis, Hibiscus sabdariffa, Lonicera japonica, Humulus lupulus, Aesculus hippocastanum, Equisetum arvense, Sempervivum tectorum, Hyssopus officinalis, Cetraria islandica, Baptisia tinctoria, Chondrus crispus, Hedera helix, Jasminum officinale, Simmondsia chinensis, Juniperus communis, Anthyllis vulneraria, Kigelia africana, Actinidia chinensis, Pueraria lobata, Alchemilla vulgaris, Lavandula angustifolia, Citrus limon, Cymbopogon citratus, Glycyrrhiza glabra, Lilium candidum, Citrus aurantifolia, Tilia cordata, Nelumbo nucifera, Macadamia ternifolia, Magnolia biondii, Berberis aquifolium, Malva sylvestris, Mangifera indica, Calendula officinalis, Castanea sativa, Althaea officinalis, Filipendula ulmaria, Cucumis melo, Silybum marianum, Panicum miliaceum, Colophospermum mopane, Sorbus aucuparia, Verbascum thapsus, Guazuma ulmifolia, Myrtus communis, Tropaeolum majus, Azadirachta indica, Urtica dioica, Ascophyllum nodosum, Myristica fragrans, Quercus robur, Laminaria digitata, Avena sativa, Usnea barbata, Olea europaea, Allium cepa, Citrus sinensis, Mentha citrata, Origanum vulgare, Viola tricolor, Carica papaya, Capsicum annuum, Petroselinum crispum, Passiflora incarnata, Prunus persica, Pyrus communis, Centella asiatica, Paeonia officinalis, Piper nigrum, Mentha piperita, Ananas comosus, Prunus domestica, Punica granatum, Pulmonaria officinalis, Cucurbita pepo, Cydonia oblonga, Rubus idaeus, Trifolium pratense, Oryza sativa, Aspalathus linearis, Rosa centifolia, Rosmarinus officinalis, Secale cereale, Salvia officinalis, Schisandra chinensis, Hippophae rhamnoides, Sesamum indicum, Capsella bursa pastoris, Albizia julibrissin, Artemisia abrotanum, Mentha spicata, Triticum aestivum, Spirulina platensis, Picea abies, Hypericum perforatum, Averrhoa carambola, Stevia rebaudiana, Fragaria ananassa, Helianthus annuus, Melilotus officinalis, Tanacetum cinerariifolium, Citrus reticulata, Thymus vulgaris, Salvadora persica, Valeriana officinalis, Vanilla planifolia, Verbena officinalis, Viola odorata, Juglans regia, Nasturtium officinale, Citrullus lanatus, Triticum aestivum, Camellia sinensis, Crataegus rhipidophylla, Thymus serpyllum, Salix alba, Hamamelis virginiana, Isatis tinctoria, Lycium barbarum, Artemisia absinthium, Achillea millefolium, Hymenaea courbaril, Cananga odorata, Tricholoma matsutake Singer, Phaeophyceae* or combinations thereof.

An oil soluble extract according to the present invention is readily formed by conventional techniques such as contacting a portion of a plant such as leaves, stems, buds, roots, fruit, or combinations thereof, or a portion of algae, with a hydrophobic solvent for a period of time such as from 1 to 48 hours, and then filtering the mixture to obtain the extract. The volume ratio of solvent to plant material is typically between 1:1 and 20:1. Extraction in solvents of decreasing hydrophilicity and elution by conventional techniques allows one to produce an organic solvent-soluble extract. The organic solvent illustratively includes one or more ethers, furans, petroleum distillates, alkanes, halogenated alkanes, alcohols, acetates, and combinations thereof. After sufficient interaction between the extraction solvents, typically between 20 minutes and 48 hours, the organic phase is isolated to obtain an extract according to the present invention. Suitable sources of extracts include the aforementioned plants and algaes such red, green, and brown algaes and tuft-forming cyanobacteria collectively referred to herein as "seaweed."

Other hydrophobic liquid phase active agents include nanophase particles having surface groups that impart dispersibility in the hydrophobic liquid phase. Exemplary of such nanophase particles are zinc oxide, titanium dioxide, and combinations thereof. Surface groups that render a nanophase particle dispersible in the hydrophobic liquid phase illustratively include $C_2$-$C_{24}$ alkanes, $C_6$-$C_{24}$ aromatics, $C_3$-$C_{24}$ alkenes, and variants thereof including substituents such as $C_2$-$C_{12}$ esters, $C_2$-$C_{12}$ ethers, and $C_2$-$C_{12}$ ketones.

Each hydrophobic liquid phase active agent typically is present as 0.0001 to 10 weight percent of the hydrophobic liquid phase. It is appreciated that multiple active agents may be present in a hydrophobic liquid phase.

A hydrophilic phase that forms a meniscus with the hydrophobic liquid phase in the cosmetic composition is made up primarily of water, preferably deionized water. One or more water miscible solvents, such as $C_1$-$C_4$ alcohols, may constitute a lesser portion of the hydrophilic phase, provided that there remains a stable meniscus with the hydrophobic liquid phase.

The hydrophilic liquid phase typically constitutes from 95 to 5 volume percent of the overall cosmetic composition, with the remainder being hydrophobic liquid phase. In some embodiments, the hydrophilic liquid phase constitutes from 75 to 40 volume percent of the overall composition. In certain inventive embodiments, the hydrophilic phase does not contain synthetic substances. In other inventive embodiments, the hydrophilic phase does not contain detergents or foaming agents.

Substances may be dissolved or suspended in the hydrophilic liquid phase. These substances illustratively include anti-oxidizing agents, coloring agents, biocides, particulates, active agents intended to improve skin quality or appearance, skin moisturizers, and combinations thereof.

Hydrophilic active agents operative herein illustratively include water-soluble plant extracts from plants such as Rhododendron ferrugineum, Amaranthus caudatus, Angelica archangelica, Pimpinella anisum, Malus domestica, Mentha suaveolens, Oat avenanthramide, Prunus armeniaca, Arnika montana, Cynara scolymus, Asparagus officinalis, Persea americana, Cardiospermum halicacabum, Melissa officinalis, Bambusa vulgaris, Musa paradisiaca, Adansonia digitata, Berberis vulgaris, Ocimum basilicum, Laurus nobilis, Epilobium angustifolium, Allium ursinum, Geum urbanum, Betula pubescens, Quassia amara, Nigella sativa, Ribes nigrum, Morus nigra, Raphanus sativus, Camellia sinensis, Rubus fruticosus, Iris versicolor, Vaccinium myrtillus, Borago officinalis, Vicia faba, Menyanthes trifoliata, Fagopyrum esculentum, Arctium lappa, Ruscus aculeatus, Theobroma cacao, Acorns calamus, Carum carvi, Elettaria cardamomum, Daucus carota sativus, Erythroxylum catuaba, Centaurium erythraea, Matricaria chamomilla, Prunus cerasus, Cicer arietinum, Chlorella vulgaris, Aronia melanocarpa, Cinchona pubescens, Cinnamomum verum, Syzygium aromaticum, Cocos nucifera, Coffea arabica, Plectranthus barbatus, Tussilago farfara, Symphytum officinale, Plantago major, Coriandrum sativum, Zea mays, Papaver rhoeas, Centaurea cyanus, Gossypium herbaceum, Vaccinium vitis-idaea, Primula veris, Vaccinium macrocarpon, Cucumis sativus, Curcuma longa, Bellis perennis, Rosa damascena, Turnera diffusa, Taraxacum officinale, Phoenix dactylifera, Lamium album, Rosa canina, Hylocereus undatus, Daemonorops draco, Echinacea angustifolia, Leontopodium alpinum, Sambucus nigra, Acanthopanax senticosus, Phyllanthus emblica, Eucalyptus globulus, Oenothera biennis, Helichrysum arenarium, Euphrasia rostkoviana, Trigonella foenum-graecum, Ficus carica, Linum usitatissimum, Plumeria alba, Fumaria officinalis, Rumex acetosa, Gardenia Yessminoides, Gentiana lutea, Zingiber officinale, Ginkgo biloba, Panax ginseng, Solidago virgaurea, Vitis vinifera, Citrus paradisi, Camellia sinensis, Paullinia cupana, Graminis flos, Corylus avellana, Lawsonia inermis, Hibiscus sabdariffa, Lonicera japonica, Humulus lupulus, Aesculus hippocastanum, Equisetum arvense, Sempervivum tectorum, Hyssopus officinalis, Cetraria islandica, Baptisia tinctoria, Chondrus crispus, Hedera helix, Jasminum officinale, Simmondsia chinensis, Juniperus communis, Anthyllis vulneraria, Kigelia africana, Actinidia chinensis, Pueraria lobata, Alchemilla vulgaris, Lavandula angustifolia, Citrus limon, Cymbopogon citratus, Glycyrrhiza glabra, Lilium candidum, Citrus aurantifolia, Tilia cordata, Nelumbo nucifera, Macadamia ternifolia, Magnolia biondii, Berberis aquifolium, Malva sylvestris, Mangifera indica, Calendula officinalis, Castanea sativa, Althaea officinalis, Filipendula ulmaria, Cucumis melo, Silybum marianum, Panicum miliaceum, Colophospermum mopane, Sorbus aucuparia, Verbascum thapsus, Guazuma ulmifolia, Myrtus communis, Tropaeolum majus, Azadirachta indica, Urtica dioica, Ascophyllum nodosum, Myristica fragrans, Quercus robur, Laminaria digitata, Avena sativa, Usnea barbata, Olea europaea, Allium cepa, Citrus sinensis, Mentha citrata, Origanum vulgare, Viola tricolor, Carica papaya, Capsicum annuum, Petroselinum crispum, Passiflora incarnata, Prunus persica, Pyrus communis, Centella asiatica, Paeonia officinalis, Piper nigrum, Mentha piperita, Ananas comosus, Prunus domestica, Punica granatum, Pulmonaria officinalis, Cucurbita pepo, Cydonia oblonga, Rubus idaeus, Trifolium pratense, Oryza sativa, Aspalathus linearis, Rosa centifolia, Rosmarinus officinalis, Secale cereale, Salvia officinalis, Schisandra chinensis, Hippophae rhamnoides, Sesamum indicum, Capsella bursa pastoris, Albizia julibrissin, Artemisia abrotanum, Mentha spicata, Triticum aestivum, Spirulina platensis, Picea abies, Hypericum perforatum, Averrhoa carambola, Stevia rebaudiana, Fragaria ananassa, Helianthus annuus, Melilotus officinalis, Tanacetum cinerariifolium, Citrus reticulata, Thymus vulgaris, Salvadora persica, Valeriana officinalis, Vanilla planifolia, Verbena officinalis, Viola odorata, Juglans regia, Nasturtium officinale, Citrullus lanatus, Triticum aestivum, Camellia sinensis, Crataegus rhipidophylla, Thymus serpyllum, Salix alba, Hamamelis virginiana, Isatis tinctoria, Lycium barbarum, Artemisia absinthium, Achillea millefolium, Hymenaea courbaril,

*Cananga odorata, Tricholoma matsutake* Singer, *Phaeophyceae*, or combinations thereof.

A water soluble extract according to the present invention is readily formed by conventional techniques such as contacting a portion of a plant such as leaves, stems, buds, roots, fruit, or combinations thereof with a hydrophilic solvent for a period of time, such as from 1 to 48 hours, and then filtering the mixture to obtain the extract. The volume ratio of solvent to plant material is typically between 1:1 and 20:1. Extraction in a polar solvent produces an extract soluble in the hydrophilic phase and is conventional to the art.

According to the present invention, proteins active in skin quality improvement are used as hydrophilic liquid phase active agents. Egg hatching active proteins and in particular, fish spawn proteins having an exfoliative effect on living mammalian skin are hydrophilic liquid phase active agents in certain inventive embodiments.

A fish spawn protein isolate includes, for example, a serine proteinase (e.g., zonase), a lectin (e.g., leukolectin), a choriolysin, or a combination thereof, or crude extracts containing such proteins, and has the properties detailed in one or more of U.S. Pat. No. 6,346,245, col. 4, line 15-col. 5, line 8; US2009/0274770 [0321]-[0326], and US 2011/0280882 [0157]-[0194]. Exemplary sources of fish spawn for protein isolation include roe from sturgeon, salmon, whitefish, vendace, cod, capelin, and burbot. It is appreciated that other sources of egg proteins operative herein include amphibian egg cases, such as those of tadpoles and salamanders; reptilian egg cases; and fowl egg cases. Typically, an egg protein isolate, or with particularity, fish spawn protein isolate, that is an aqueous solution containing at least some of the above recited proteins constitutes from 0.0001 to 10% total weight of the hydrophilic liquid phase, with 0.001 to 10% of the isolate solution being protein. For example, when 0.001% of the isolate solution is protein, the amount of fish spawn protein in the hydrophilic liquid phase in some embodiments would range from 0.000000001 to 0.0001% by weight. When 10% of the isolate solution is protein, the amount of fish spawn protein in the hydrophilic liquid phase in some embodiments would range from 0.0001 to 1% by weight. In some embodiments, the amount of protein ranges even lower than 0.000000001% (e.g., 0.0000000001 to 0.000000001%), or is higher than 1% (e.g., 1 to 2%, 1 to 3%, 1 to 4%, or 1 to 5%). It is appreciated that the amount of protein present in an inventive cosmetic composition depends on factors illustratively including miscibility with other components and the amount needed to produce the desired effect.

Other hydrophilic liquid phase active agents include nanophase particles having surface groups that impart dispersibility in the hydrophilic liquid phase. Exemplary of such nanophase particles are zinc oxide and titanium dioxide, and combinations thereof. Surface groups that render a nanophase particle dispersible in the hydrophilic liquid phase illustratively include hydroxyl groups, amine groups, $C_2$-$C_6$ alcohols, $C_1$-$C_8$ carboxylates, $C_2$-$C_{12}$ quaternary amines and $C_2$-$C_6$ sulfonates.

Still other hydrophilic liquid phase active agents include skin brighteners such as hydroquinones; undecylenoyl phenylalanine; mushroom extracts, specifically including extract of Songyi mushroom (botanical name *Tricholoma matsutake* Singer); and combinations thereof; bleaching agents; vitamins such as Vitamin C and derivatives thereof such as ascorbyl glucoside or sodium or magnesium ascorbyl phosphate, Vitamin E and derivatives thereof such as acetates, and Vitamin K; and combinations thereof.

In some inventive embodiments, a particulate composition is suspended in the hydrophilic liquid phase. Suspended particles operative herein illustratively include mica, titanium dioxide, zinc oxide, silicon dioxide, tin oxide, iron oxide, fluorphlogopite, gold leaf specks, metalized plastic flakes, and combinations thereof. Inclusion of such particles in the cosmetic composition may be for any of several reasons, including aesthetics and a sun screen effect. For example, they may delineate the globules produced on mixture of the hydrophobic and hydrophilic liquid phases, and/or they may impart a sparkle effect on user skin. Suspended particulate, when present, is present in amounts of between 0.03 and 0.20 weight percent of the hydrophilic liquid phase. In still further inventive embodiments, a suspending agent is added to slow the settling of suspended particulate from the hydrophilic phase. Suspending agents operative herein illustratively include *sclerotium* gum, xanthan gum, guar gum, salts of carboxymethylcellulose, carrageenan, carbomer, acrylate polymers/copolymers, and combinations thereof. The suspending agent, when present, is present in amounts of between 0.10 and 3.0 weight percent of the hydrophilic liquid phase.

Each hydrophilic liquid phase active agent typically is present from 0.0001 to 10 weight percent of the hydrophilic liquid phase, with the exception that hydrophilic liquid phase proteinaceous active agents are typically each present from 0.0000001 to 1 weight percent of the hydrophilic liquid phase. Other operable ranges for the active agent, including a proteinaceous active agent, are 0.000001% to 10%, 0.00001% to 10%, 0.00001% to 1%, and 0.0000001% to 0.1%. It is appreciated that the hydrophilic liquid phase may contain multiple active agents.

Formulation of an inventive biphasic cosmetic composition containing active protein(s) requires that the proteins be exposed to a limited range of pH values, limited (if any) shear mixing, and limited (if any) heat in the process of making the composition, including during hydrophilic liquid phase formation. To maintain exfoliative enzymatic activity of proteins, a process of cosmetic formulation includes buffering of the hydrophilic phase to a pH of between 5.6 and 8 prior to introduction of the protein to that phase. Buffering is commonly practiced in the field and includes the addition of an acid, a base, a salt of the acid, or a combination thereof to equilibrate an aqueous solution or aqueous phase of an emulsion to a desired pH. It is appreciated that pH measurement is routine and measured quantitatively via volumetric titration or with potentiometric electrodes such as those commercially available from Thermo Fisher Scientific (Waltham Mass., USA). Alternatively, pH may be measured qualitatively with litmus paper kits.

Microbial degradation of proteins in the composition may occur due to organisms present during formulation or those introduced during usage of a multiple dose container through subject contact with an inventive biphasic cosmetic. Growth of such microbes can be inhibited by including in the composition a broad spectrum biocide or a combination of biocides. A broad spectrum biocide is defined herein as having activity against Gram positive bacteria, Gram negative bacteria, yeasts and fungi associated with a healthy human subject. Biocides operative herein illustratively include benzoic acid, parabens, salicylic acid, carbolic acid, sorbic acid, alkyl p-hydroxybenzoates, p-chlorometacresol, hexachlorophene, benzalkonium chloride, chlorohexidine chloride, trichlorocarbanilide, phenoxyethanol, acylsarcosines, glutathione, malic acid, tartaric acid, ascorbic acid, ascorbates, essential plant oils, mutacin proteins, and combinations thereof. In certain embodiments of the present invention, only naturally-derived biocides are present. Naturally-derived biocides illustratively include fermentation filtrates such as those of *Lactobacillus, Streptococcus mutans*, and *Leuconostoc*; bisabolol; eucalyptol; thymol; inositol; saponins; polyepsilon-lysine; and natural extract of plants, such as Japanese honeysuckle (*Lonicera japonica*), yangti (*Rumex japonicus*), kushen (*Sophora flavescens*), candock, wild oregano, orange, sage, manifoil, common mallow, chuanxiong (*Cnidii officinale* Makino), Japanese green gentian (*Swertia japonica* Makino), bisabolol, thyme, dang gui (*Angelica sinensis*), orange peel, birch, field horsetail, dishcloth gourd, horse chestnut tree, creeping saxifrage (*Saxifrage stolonifera*), arnica, lily, mugwort, peony, aloe, *gardenia*, as well as those detailed in M. M. Cowan, Clinical Microbiology Reviews, 12(4) October 1999, p. 564-582; or combinations thereof. Such extracts are obtained by procedures detailed in Clinical Microbiology Reviews, 12(4) October 1999, pages 573-574, e.g., using a hydrophilic organic solvent such as a $C_1$-$C_8$ alcohol, or using polyhydric alcohols, water, or aqueous alcohols. In a specific inventive embodiment, *Lactobacillus* fermentation filtrates and polyepsilon-lysine are used as naturally derived biocides, each alone or in combination. It is appreciated that, in addition to biocide properties, a natural extract often imparts a fragrance to an inventive cosmetic. A biocide is present in multi-use packages of inventive biphasic cosmetics in specific embodiments from 0.1 to 5 total weight percent. It is appreciated that quantities of biocides beyond 5 total weight percent are readily included as desired.

An inventive biphasic cosmetic hydrophilic phase is, in certain embodiments, pH buffered to a value of between 5.6 and 7.9, and in other embodiments to between 6.5 and 6.8, while in still in other embodiments to between 6.8 and 7.3, or between 5.0 and 6.4, or between 5.6 and 6.4.

An inventive biphasic cosmetic is readily formed by combining premixed hydrophilic and hydrophobic phases in various ratios, such as approximately 1:1 or 4:3 or 3:4, to form a layered composition. Alternatively, the water and hydrophobic solvent can be combined to form a layered composition to which the remaining ingredients are added, together or in sequence, with agitation to facilitate segregation of each ingredient into the appropriate phase. A process of improving skin appearance is provided that includes application of an inventive composition to the skin of a mammal 1-10 times daily, or at least three times per week, to achieve improvement of skin appearance.

An attribute of the present invention is that, upon agitation, the biphasic cosmetic temporarily forms kinetically unstable globules made up of the two phases, thereby allowing user to apply both phases in an amount that reflects the proportion of each phase in the overall cosmetic composition. The globule size is rendered smaller with additional agitation. Typical globule sizes that facilitate ease of application to skin range from 0.1 millimeter (mm) to 5 mm.

A summary of the typical ranges of ingredients for inventive biphasic cosmetic compositions is provided in Table 1.

TABLE 1

Typical ranges of ingredients, where percentages are expressed in weight percent of the given phase.

Hydrophobic phase (40% to 60% of the overall biphasic mix)

| | |
|---|---|
| hydrophobic solvent | Remainder |
| active agent(s), each | 0 to 10% |
| suspended particulate | 0.01 to 5% |
| coloring agents | 0.01 to 1% |
| anti-oxidizing agents | 0.01 to 2% |
| biocide | 0.1 to 5% |
| perfumes | 0.01 to 1% |

Hydrophilic phase (40% to 60% of the overall biphasic mix)

| | |
|---|---|
| hydrophilic solvent | Remainder |
| active agent(s), each | 0.0001 to 10% |
| protein active agents | 0.0000001 to 1% |
| suspended particulate | 0.01 to 5% |
| buffering agent | 0.2 to 5% |
| suspending agent | 0.1 to 3% |
| coloring agents | 0.01 to 1% |
| anti-oxidizing agents | 0.01 to 2% |
| biocide | 0.1 to 5% |
| perfumes | 0.01 to 1% |

The present invention is further illustrated with reference to the following non-limiting examples.

Example 1

A biphasic cosmetic is made by combining a hydrophobic phase and a hydrophilic phase.

The hydrophobic phase is created by adding 1 to 10 grams of an algae extract in capric/caprylic triglyceride to between 90 to 99 grams of squalane.

An aqueous hydrophilic phase is created by adding 0.1 to 0.4 grams of *sclerotium* gum to 75 ml of hot water (80° C.) and homogenizing to a uniform solution. The solution is cooled to 50° C. and 3 ml of *Lactobacillus* fermentation filtrate added, followed sequentially by buffered polyepsilon-lysine buffer solution containing 2 grams ascorbyl glucoside, 0.1 grams of *Crocus sativus* flower extract, 0.1 grams of gold flecks and inorganic glitter formed of titanium dioxide, tin oxide, iron oxide and fluorophlogopite or mica. The hydrophilic phase is pH adjusted to a pH between 6.5 and 7.3. Six ml of salmon hatching fluid filtrate containing zonase, lectin and choriolysin proteins is then added to complete a hydrophilic phase.

Approximately equal volumes of the hydrophilic and hydrophobic phases are then combined to form the biphasic cosmetic. (The ratio is about 4:3 by weight.) The biphasic cosmetic is packaged in a glass vial. With vigorous shakes of the vial, globules containing one of the phases become suspended in the other phase; these are then immediately applied to user skin. The resulting biphasic cosmetic composition is effective in moisturizing skin, exfoliation, and adding a sparkle to applied skin.

Example 2

A biphasic cosmetic is formed as detailed in Example 1, with the addition of hydrophobic colloidal zinc oxide to the hydrophobic liquid phase in an amount constituting 0.5 weight percent of that phase. The resulting cosmetic has sun screen properties.

Example 3

A biphasic cosmetic is formed as detailed in Example 1, with the addition of hydrophobic polyvinylpyrrolidone terminated colloidal silver to the hydrophobic liquid phase, in an amount constituting 0.1 weight percent of that phase. The resulting cosmetic has anti-bacterial properties on skin.

Example 4

The salmon hatching fluid filtrate used in Example 1 is obtained from Aqua Bio Technology AS and produced by a procedure as detailed in U.S. Pat. No. 6,346,245, examples 1-4.

Example 5

A biphasic cosmetic is made by combining a hydrophobic phase and a hydrophilic phase. The hydrophobic phase is created by adding 1 gram of an algae extract in capric/caprylic triglyceride to 99 grams of squalane. An aqueous hydrophilic phase is created by adding 0.23 grams of *sclerotium* gum to 75 ml of hot water (80° C.) and homogenizing to a uniform solution. The solution is cooled to 55° C. and 3 ml of *Lactobacillus* fermentation filtrate added, followed sequentially by polyepsilon-lysine buffer solution. In a separate vessel, 5 grams of water are premixed with 2 grams of ascorbyl glucoside. The pH in the separate vessel is adjusted with 20% sodium hydroxide to pH 6.5 to 6.8, and then the contents of the separate vessel are added to the batch and mixed until uniform. In a separate vessel, 0.1 grams of *Crocus sativus* flower extract, 0.1 grams of gold flecks and inorganic glitter formed of titanium dioxide, tin oxide, iron oxide and fluorophlogopite or mica are mixed with 6 ml of salmon hatching fluid filtrate containing zonase, lectin and choriolysin proteins and added to the batch and mixed until uniform. The hydrophilic phase is pH adjusted to a pH between 6.5 and 7.3.

Approximately equal volumes of the hydrophilic and hydrophobic phases are then combined to form the biphasic cosmetic. The biphasic cosmetic is packaged in a glass vial. With vigorous shakes of the vial, globules of one phase are suspended in the other phase (typically the globules are made up of hydrophobic (squalane) phase). The globule-containing product is immediately applied to user skin. The biphasic cosmetic composition is effective in moisturizing, exfoliation, and adding a sparkle to skin.

Example 6

A biphasic cosmetic is made by combining a hydrophobic phase and a hydrophilic phase. The hydrophobic phase is created by adding 1 gram of an algae extract in capric/caprylic triglyceride to 99 grams of squalane. An aqueous hydrophilic phase is created by adding 0.23 grams of *sclerotium* gum to approximately 78-79 ml of hot deionized water (80° C.) and homogenizing to a uniform solution. The solution is cooled to 55° C. and 3 grams of *Lactobacillus* fermentation filtrate added, followed sequentially by polyepsilon-lysine/citric acid buffered solution. In a separate vessel, 5 grams of water are premixed with 2 grams of ascorbyl glucoside, 0.10 grams citric acid and 1.0 gram sodium citrate. The pH in the separate vessel is adjusted with 20% sodium hydroxide to pH 6.5 to 6.8, and then the contents of the separate vessel are added to the batch and mixed until uniform. 0.1 grams of *Crocus sativus* flower extract, 0.08 grams of glitter blend composed of gold flecks, titanium dioxide, tin oxide, iron oxide and fluorophlogopite or mica, and 6 ml of salmon hatching fluid filtrate containing zonase, lectin and choriolysin proteins are added to the batch and mixed until uniform. The hydrophilic phase is pH adjusted to a pH between 6.5 and 7.3 and is adjusted to 100 grams final weight by adding enough deionized water and mixing until uniform.

Comparative Example

A biphasic mixture is prepared by adding 1 gram of capric/caprylic triglyceride to 99 grams of squalane, and then combining this hydrophobic phase with water buffered to pH 6.5 to 6.8, in an approximately 1:1 ratio by volume (approximately 3:4 by weight).

Example 7

A separation study was conducted to determine the time needed for intermixed phases to separate. A cosmetic mixture as described in Example 6 was shaken manually for 3 minutes until well mixed and then separated into three individual 20 ml clear glass vials. Likewise, the mixture of the Comparative Example was shaken manually for 3 minutes until well mixed and then separated into three individual 20 ml clear glass vials. After 3 minutes of mixing manually, the vials were placed on a table in an upright position at time zero. Using a calibrated stopwatch, the time is recorded from time zero to when each sample began to separate into layers. The cosmetic mixture of Example 6 had an average separation time of 499 seconds. The Comparative Example had an average separation time of 21.8 seconds. This shows that the cosmetic mixture of Example 6 provides a sufficiently stable mixture after shaking to allow time for application of the unseparated mixture to skin.

Example 8

To measure the stability of the mixed biphasic cosmetic composition, zeta potential was determined with roughly 2 ml of each mixture (a mixture of the Example 6 composition and a mixture of the Comparative Example) in a thoroughly mixed condition produced by manually shaking for 3 minutes. Data points were obtained for a total of five runs at three minutes per run for a total of 15 minutes of data collection. Both the Example 6 composition and the Comparative Example on average had neutral surface charge (or zeta potential) of 0 millivolts in between the surfaces of the oil droplets in each respective biphasic composition, indicating that the oil droplets were an unstable dispersion that returns to a separated state.

Example 9

The relative size distribution of the oil droplets produced after shaking the two compositions was determined by diluting one drop from each shaken composition in 20 ml of ultrapure deionized water. Data points were obtained for a total of five runs at three minutes per run for a total of 15 minutes of data collection using acoustic sensors during the measurement of zeta potential. Oil droplets of roughly 6.6 µm diameter are produced upon shaking the composition of Example 6. In contrast, much larger (11.3 µm diameter) oil droplets are produced upon shaking the composition of the Comparative Example. Because of the smaller oil droplet size, a biphasic cosmetic as described in Example 6 can be applied more evenly to skin than can the Comparative Example.

Example 10

The rate of water loss of a mixture of the Example 6 composition and of a mixture of the Comparative Example was determined by placing roughly one gram of each product onto a non-porous aluminum substrate kept at 25° C.

The mass of each sample was recorded at 0, 240 minutes and 360 minutes, using a calibrated four decimal place balance. The mixture of Example 6 lost water due to evaporation at roughly 1.3 mg/min. The mixture of the Comparative Example lost water due to evaporation at roughly 0.5 mg/min. As a result, a biphasic cosmetic as described in Example 6 is expected to deliver hydrophilic ingredients to applied skin more quickly than would the Comparative Example.

Any patents or publications mentioned in this specification are herein incorporated by reference to the same extent as if each individual publication was specifically and individually indicated to be incorporated by reference.

The foregoing description is illustrative of particular embodiments of the invention, but is not meant to be a limitation upon the practice thereof.

The invention claimed is:

1. A bi-phasic, non-emulsion cosmetic composition for application to skin comprising, together in one container:
   a hydrophobic liquid phase comprising squalane as a hydrophobic solvent;
   a hydrophilic liquid phase separate from the hydrophobic liquid phase and having a meniscus in contact with said hydrophobic phase;
   a first active agent in said hydrophobic liquid phase or said hydrophilic liquid phase; and
   *sclerotium* gum present in said hydrophilic liquid phase.

2. The cosmetic composition of claim 1, wherein said hydrophobic liquid phase is present in the composition from 25 to 60 volume percent.

3. The cosmetic composition of claim 1, wherein the first active agent is an algae extract.

4. The cosmetic composition of claim 1, wherein said first active agent is a protein soluble in said hydrophilic liquid phase.

5. The cosmetic composition of claim 4, wherein said protein is an enzyme having activity on human skin.

6. The cosmetic composition of claim 1, wherein said first active agent is a fish spawn protein isolate from hatching fish eggs.

7. The cosmetic composition of claim 1, further comprising an insoluble particulate present in said hydrophilic liquid phase.

8. The cosmetic composition of claim 1, wherein the composition does not contain a foaming agent.

9. The cosmetic composition of claim 1, further comprising a particulate selected from the group consisting of mica, gold flakes, metalized plastic flakes, fluorphlogopite, titanium dioxide, tin oxide, red iron oxide, and combinations of any two or more from the group.

10. The cosmetic composition of claim 1, further comprising a second active agent soluble in one of the phases, wherein one of the first and second active agents is soluble in the hydrophobic liquid phase, and the other of the first and second active agents is soluble in the hydrophilic liquid phase.

11. The cosmetic composition of claim 1, wherein said hydrophilic phase has a pH of between 5.6 and 7.9.

12. The cosmetic composition of claim 1, wherein the *sclerotium* gum is present in the hydrophilic liquid phase in a proportion of 0.23 grams *sclerotium* gum per 100 grams hydrophilic liquid phase.

13. The cosmetic composition of claim 1, further comprising a *Lactobacillus* fermentation filtrate.

14. A bi-phasic, non-emulsion cosmetic composition for application to skin, the composition comprising:
   a hydrophobic liquid phase comprising squalane as a hydrophobic solvent;
   in contact with the hydrophobic liquid phase, a hydrophilic liquid phase comprising water as a hydrophilic solvent; and
   *sclerotium* gum and protein dissolved in the hydrophilic liquid phase.

15. The cosmetic composition of claim 14, further comprising at least one biocide.

16. The cosmetic composition of claim 14, wherein said protein is comprised in a fish spawn protein isolate from hatching fish eggs.

17. The cosmetic composition of claim 16, wherein said fish spawn protein isolate comprises choriolysin, a serine protease, a lectin, or a combination thereof.

18. The cosmetic composition of claim 16, wherein said fish spawn protein isolate is derived from salmon roe.

19. The cosmetic composition of claim 14, wherein the hydrophobic liquid phase comprises an algae extract, capric triglyceride, caprylic triglyceride, or a combination thereof.

20. The cosmetic composition of claim 14, comprising a solid particulate suspended in the hydrophilic liquid phase.

21. The cosmetic composition of claim 14, wherein the hydrophilic liquid phase comprises a solid particulate selected from the group consisting of mica, gold flakes, metalized plastic flakes, fluorphlogopite, titanium dioxide, tin oxide, iron oxide, and combinations of any two or more thereof.

22. The cosmetic composition of claim 14, further comprising a *Lactobacillus* fermentation filtrate.

23. A biphasic, non-emulsion cosmetic composition comprising a hydrophobic phase in contact with an aqueous hydrophilic phase,
   wherein the hydrophobic phase comprises squalane, an algae extract, and caprylic/capric triglyceride; and the aqueous hydrophilic phase comprises *sclerotium* gum, *Lactobacillus* fermentation filtrate, polyepsilon-lysine, ascorbyl glucoside, *Crocus sativus* flower extract, salmon hatching fluid filtrate, and a particulate comprising gold flecks and inorganic glitter formed of titanium dioxide, tin oxide, iron oxide, and either fluorphlogopite or mica.

24. A process for applying an active ingredient to skin, comprising:
   providing the bi-phasic, non-emulsion cosmetic composition of claim 1;
   agitating the composition to form a mixture comprising globules of the hydrophobic phase suspended in the hydrophilic phase; and
   applying the mixture to skin.

25. A process for applying a protein to skin, comprising:
   providing the bi-phasic, non-emulsion cosmetic composition of claim 14;
   agitating the composition to form a mixture comprising globules of the hydrophobic phase suspended in the hydrophilic phase; and
   applying the mixture to skin.

26. A process for preparing the bi-phasic, non-emulsion cosmetic composition of claim 1, the process comprising:
   providing a hydrophobic liquid phase comprising squalane as a hydrophobic solvent, and a separate hydrophilic liquid phase comprising *sclerotium* gum, wherein at least one of the two phases contains an active agent; and
   introducing both phases into a container to form the bi-phasic, non-emulsion cosmetic composition of claim 1, with one phase layered on the other.

27. The process of claim 26, wherein the active agent is a fish spawn protein from hatching fish eggs.

28. The process of claim 26, wherein the cosmetic comprises a particulate ingredient that imparts sparkle to the composition.

* * * * *